US00PP14220P29

(12) United States Plant Patent
Bradford

(10) Patent No.: US PP14,220 P2
(45) Date of Patent: Oct. 7, 2003

(54) PLUM TREE NAMED 'SEPTEMBER YUMMY®'

(50) Latin Name: *Prunus salicina*
Varietal Denomination: 'September Yummy®'

(76) Inventor: Lowell Glen Bradford, 12439 E. Savana Rd., Le Grand, CA (US) 95333

( * ) Notice: Subject to any disclaimer, the term of this patent is extended or adjusted under 35 U.S.C. 154(b) by 0 days.

(21) Appl. No.: 10/300,578

(22) Filed: Nov. 21, 2002

(51) Int. Cl.[7] ..... A01H 5/00
(52) U.S. Cl. ..... Plt./184
(58) Field of Search ..... Plt./184

(56) References Cited

U.S. PATENT DOCUMENTS

PP8,498 P 12/1993 Bradford

*Primary Examiner*—Bruce R. Campell
*Assistant Examiner*—Susan B. McCormick

(57) ABSTRACT

The present invention relates to a plum tree, *Prunus salicina*, and more particularly to a new and distinct variety broadly characterized by a large size, vigorous, hardy, heavy blooming, pollen abundant self-unfruitful and usually productive tree. The present variety requires cross pollinization from another plum that blooms during the mid season, such as 'Santa Rosa' (unpatented). The fruit matures under the ecological conditions described during the second week in September, with first picking on Sep. 10, 2002. The fruit is uniformly medium in size, nearly full red in skin color, semi-freestone in type, yellow with some red bleeding in flesh color, very firm in texture, very good in flavor, and holds well in cold storage for more than forty days. The variety was developed using an unnamed plum seedling as the selected pollen parent and 'Bradgreen' (U.S. Plant Pat. No. 8,498) as the selected pollen parent.

1 Drawing Sheet

Botanical classification: *Prunus salicina.*
Variety denomination: 'SEPTEMBER YUMMY®'.

BACKGROUND OF THE VARIETY

In a continuing effort to improve the quality of shipping fruits, I, the inventor, typically hybridize a large number of peach, nectarine, plum, apricot, and cherry seedlings each year. I also grow a lesser number of open pollinated seeds of each of these fruits. The present invention relates to a new and distinct variety of plum tree, which has been denominated varietally as 'SEPTEMBER YUMMY®'. YUMMY® is a U.S. Trademark, application Ser. No. 75/618,722, owned by Johnny Appleseed Holdings Limited, Saint Georges Road South RD2, Hastings, New Zealand. Permission to use has been granted to the applicant by contract.

The present variety was hybridized by me in 1996, germinated and grown as a seedling on its own root in my greenhouse, and upon reaching dormancy transplanted to a cultivated area of my experimental orchard at Bradford Farms near Le Grand, Calif. in Merced County (San Joaquin Valley). Specifically, the variety was developed as a first generation cross using an unnamed plum seedling as the selected seed parent and 'Bradgreen' (U.S. Plant Pat. No. 8,498) as the selected pollen parent. Subsequent to origination of the present variety of plum tree, I asexually reproduced it by budding and grafting in the experimental orchard described above, and such reproduction of plant and fruit characteristics were true to the original plant in all respects. The reproduction of the variety included the use of 'Nemaguard' (unpatented) rootstock upon which the present variety was compatible and true to type.

The present variety is similar to its pollen parent, 'Bradgreen' (U.S. Plant Pat. No. 8,498), by being self-unfruitful and by producing plums that are sweet in flavor, firm in texture, and that mature in the late season, but is very distinguished therefrom and an improvement thereon by producing plums that are red instead of green in skin color, that are slightly oblong instead of oblate in shape, and that mature about twenty-five days later.

The present variety is most similar to 'Fortune' (unpatented) plum by being self-unfruitful and producing plums that are somewhat elongated in shape, nearly full red in skin color, and firm in texture, but is distinguished therefrom and an improvement thereon by producing plums that are sweeter in flavor and ripen about fifty days later.

SUMMARY OF VARIETY

The present plum variety is characterized by a large size, vigorous, hardy, and usually productive tree. Being self-unfruitful, the present variety requires cross pollinization from another plum that blooms during the mid season, such as 'Santa Rosa' (unpatented). The present variety's abundance of blossoms and pollen entices strong bee activity to facilitate pollination. The fruit matures under the ecological conditions described during the second week in September, with first picking on Sep. 10, 2002. The fruit is uniformly medium in size, nearly full red in skin color, semi-freestone in type, yellow with some red bleeding near the skin in flesh color, very firm in texture, very good in flavor, and holds well in cold storage for more than forty days.

DRAWING

The accompanying photograph exhibits four whole fruits positioned to display the characteristics of the skin color and form, one fruit divided transversely to the suture plane to reveal the flesh and stone, and typical leaves.

DETAILED BOTANICAL DESCRIPTION

Referring now more specifically to the pomological characteristics of this new and distinct variety of plum tree, the following has been observed under the ecological conditions prevailing near Le Grand, Merced County (San Joaquin Valley), Calif., and was developed at the state of shipping ripe on Sep. 12, 2002, on the original tree during its sixth growing season. All major color code designations are by reference to the Inter-Society Color Council, National Bureau of Standards. Common color names are also used occasionally.

Tree

Size: Large, reaching and maintaining a height of 13' [4.0 m.] and a spread of 9' [2.7 m.] after six growing seasons utilizing typical dormant pruning.

Vigor: Vigorous, responding typically to irrigation and fertilization. The variety grows about 4' [1.2 m.] of surplus top-growth during the spring and summer. The plant should be grown on a standard commercial rootstock for production purposes.

Growth: Upright and dense.

Form: Vase formed.

Hardiness: Hardy with respect to central California winters.

Heat tolerance: Observed to perform adequately in typical central California climatic conditions, which typically include prolonged periods of heat.

Drought tolerance: Variety is developed for commercial orchards and requires regular irrigation.

Production: Very productive, thinning usually necessary.

Fertility: Self-unfruitful, requiring cross pollination by a suitable mid seasonal blooming plum, such as 'Santa Rosa' (unpatented).

Bearing: Usually consistent, but some uncertainty exists if inclement weather is encountered during the blooming period.

Trunk:

- *Size.*—Medium, reaching a maximum diameter of 3¾" [95 mm.] after the sixth growing season.
- *Texture.*—Shaggy.
- *Bark color.*—Dark grayish brown [62. d.gy.Br] with Light brown [57. l.Br] crevices streaked throughout.
- *Lenticels.*—Approximate Number Per Square Inch: 12. Color: Dark orange yellow [72. d.OY]. Typical Size: ⅛" to ⅜" [3.2–9.5 mm.].

Branches:

- *Size.*—Diameter of limb is 1½" [38 mm.] measured 12" above the secondary fork, typical of *Prunus salicina*, and dependent upon cultural practices and climatic conditions.
- *Texture.*—Smooth on first and second year wood, increasing roughness with age.
- *Color.*—1st Year Wood Topside: Deep brown [56. deep Br] when exposed to sunlight. 1st Year Wood Underside: Strong yellow green [117. s.YG]. Older Wood: Deep brown [56. deep Br].
- *Lenticels.*—Approximate Number Per Square Inch: 50. Color: Dark orange yellow [72. d.OY]. Typical size: 1/16" to 3/16" [1.6–4.8 mm.].

Leaves:

- *Size.*—Large. Average Length: 4¼" [108 mm.]. Average width: 2⅛" [54 mm.].
- *Arrangement.*—Alternate.
- *Thickness.*—Medium.
- *Form.*—Elliptical.
- *Apex.*—Acute to somewhat acuminate.
- *Base.*—Acute with an average angle base angle of seventy-five degrees.
- *Surface.*—Smooth.
- *Color.*—Dorsal Surface: Moderate olive green [125. m.OlG]. Ventral Surface: Moderate yellow green [120. m.YG].
- *Margin.*—Finely serrate.
- *Venation.*—Pinnately net veined.
- *Petiole.*—Average Length: ¾" [19.1 mm.]. Average Thickness: 1/16" [1.6 mm.]. Color: Light yellow green [119. l.YG] becoming Dark purplish red [259. d.pR] with aging and exposure to sunlight.
- *Stipules.*—Number: 2 per leaf, up to 6 per growing tip. Average Length: ⅜" [9.5 mm.]. Color: Brilliant yellow green [116. brill.YG] becoming Dark grayish reddish brown [47. d.gy.rBr] with age.
- *Glands.*—Number: 1 to 4, most often 2. Position: Usually alternate, positioned mostly on the petiole. Size: Small. Form: Globose. Color: Brilliant yellow green [116. brill.YG] becoming Deep reddish brown [41. deep rBr] in the center with age.
- *Leaf buds.*—Conic.

Flower buds:

- *Hardiness.*—Hardy, with respect to central California winters.
- *Diameter.*—Typically 3/16" [4.8 mm.] 1 week before bloom.
- *Length.*—Typically ⅜" [9.5 mm.] 1 week before bloom.
- *Form.*—Not appressed.
- *Surface.*—Pubescent.
- *Color.*—White [263. White].

Flowers: Perfect, complete, perigynous, usually a single pistil, typically twenty-eight or more stamens, five sepals and petal locations alternately positioned.

- *Average flower diameter.*—¾" [19.1 mm.].
- *Number of petals.*—Five, no double blossoms observed.
- *Petal shape.*—Oval, slightly concave inwardly.
- *Petal margin.*—Somewhat wavy.
- *Average petal diameter.*—⅜" [9.5 mm.].
- *Average petal length.*—7/16" [11.1 mm.].
- *Petal apex.*—Rounded.
- *Petal base.*—Rounded.
- *Petal color.*—White [263. White].
- *Anther color.*—Brilliant yellow [83. brill.Y].
- *Stigma color.*—Light greenish yellow [101. l.gY].
- *Sepal color.*—Light yellow green [119. l.YG].
- *Sepal length.*—5/32" [4 mm.].
- *Sepal width.*—⅛" [3 mm.].
- *Average pistil length.*—7/16" [11.1 mm.].
- *Average stamen length.*—⅜" [9.5 mm.].
- *Fragrance.*—Moderate.
- *Pollen production.*—Abundant.
- *Blooming period.*—Medium compared with other varieties, a few days before 'Santa Rosa' (unpatented).
- *Onset of bloom.*—One percent on Feb. 20, 2002.
- *Date of full bloom.*—Mar. 2, 2002.
- *Duration of bloom.*—One to two weeks, dependent on ambient temperature.
- *Number per cluster.*—Typically 3 or 4, up to 8 observed.

FRUIT

Maturity when described: Shipping ripe, Sep. 12, 2002.

Date of first picking: Sep. 10, 2002.

Date of last picking: Sep. 25, 2002.
Size: Uniform, medium.
*Average diameter axially.*—2 9/16" [65.1 mm.].
*Average diameter across suture plane.*—2½" [63.5 mm.].
*Typical weight.*—5.7 ounces [162 grams].
Form: Uniform, mostly symmetrical, globose to slightly oblong.
*Longitudinal section form.*—Oval.
*Transverse section through diameter.*—Circular.
Suture: A shallow groove extending from the base to just beyond the apex with a slight depression before the pistil point.
Ventral surface: Rounded, slightly lipped toward the apex.
Lips: Slightly unequal.
Cavity: Flaring, slightly elongated in the suture plane.
*Depth.*—½" [12.7 mm.].
*Breadth.*—1" [25.4 mm.].
Base: Truncate, but slightly cuneate when viewed along the suture.
Apex: Rounded.
Pistil point: An inconspicuous dot.
Stem: Medium.
*Average length.*—7/16" [11.1 mm.].
*Average width.*—3/32" [2.4 mm.].
Skin:
*Thickness.*—Medium.
*Surface.*—Smooth.
*Tenacity.*—Tenacious to flesh.
*Astringency.*—Slight.
*Tendency to crack.*—None observed.
*Color.*—Dark red [16. d.R] smoothly blending to Moderate red [15. m.R] over an occasional Brilliant greenish yellow [98. brill.gY] area where sun protected and Light orange yellow [70. l.OY] freckling throughtout.
*Bloom.*—Abundant.
Flesh:
*Color.*—Light yellow [86. l.Y] from the stone to near the skin where approximately ¼" of Deep red [13. deep R] bleeding occurs, increasing with maturity.
*Surface of pit cavity.*—Covered with vary short Grayish yellow [90. gy.Y] fibers that release from the stone when strongly twisted.
*Amygdalin.*—Moderate.
*Juice.*—Abundant, rich.
*Texture.*—Very firm, crisp.
*Fibers.*—Abundant, fine.
*Ripens.*—Slightly earlier toward the apex.
*Flavor.*—A tasty blend of acid and sugar, typically 19 brix.
*Aroma.*—Slight.
*Eating quality.*—Very good.

STONE

Type: Semi-freestone.
Form: Oval
Hilum: Very narrow.
Base: Straight.
Apex: Acute with an average angle of 80 degrees and a sharp tip 1/16" [1.6 mm.] in length.
Sides: Equal.
Surface: Rough.
External color of stone: Moderate olive brown [95. m.OlBr.].
Pit wall color when cracked: Light yellowish brown [76. l.yBr].
Cavity surface color: Deep yellowish brown [75. deep yBr].
Average pit wall thickness: 1/16" [1.6 mm.]
Average width: 9/16" [14.3 mm.].
Average length: ⅞" [22.2 mm.].
Average breadth: ⅜" [9.5 mm.].
Tendency to split: Very slight.
Kernel:
*Form.*—Oval.
*Pellicle color.*—Moderate yellowish brown [77. m.yBr].
*Skin color.*—Strong yellowish brown [74. s.yBr].
*Taste.*—Bitter.
*Viable.*—Yes.
*Average width.*—7/16" [11.1 mm.].
*Average length.*—9/16" [14.3 mm.].
*Amygdalin.*—Abundant.

USE

Market: Fresh market and long distance shipping.
Keeping quality: Excellent. Fruit quality observed to remain in good condition in after 40 days in standard cold room at 36° Fahrenheit [2° Celsius].
Shipping quality: Excellent.
Resistance to insects: No unusual susceptibilities noted.
Resistance to diseases: No unusual susceptibilities noted.

Other Notes

Although the new variety of plum tree possesses the described characteristics under the ecological conditions at Le Grand, Calif., in the central part of the San Joaquin Valley, it is to be expected that variations in these characteristics may occur when farmed in areas with different climatic conditions, different soil types, and/or varying cultural practices.

I claim:

1. A new and distinct variety of plum tree, substantially as illustrated and described, that is most similar to 'Fortune' (unpatented) plum by being self-unfruitful and producing plums that are somewhat elongated in shape, nearly full red in skin color, and firm in texture, but is distinguished therefrom and an improvement thereon by producing plums that are sweeter in flavor and ripen about fifty days later.

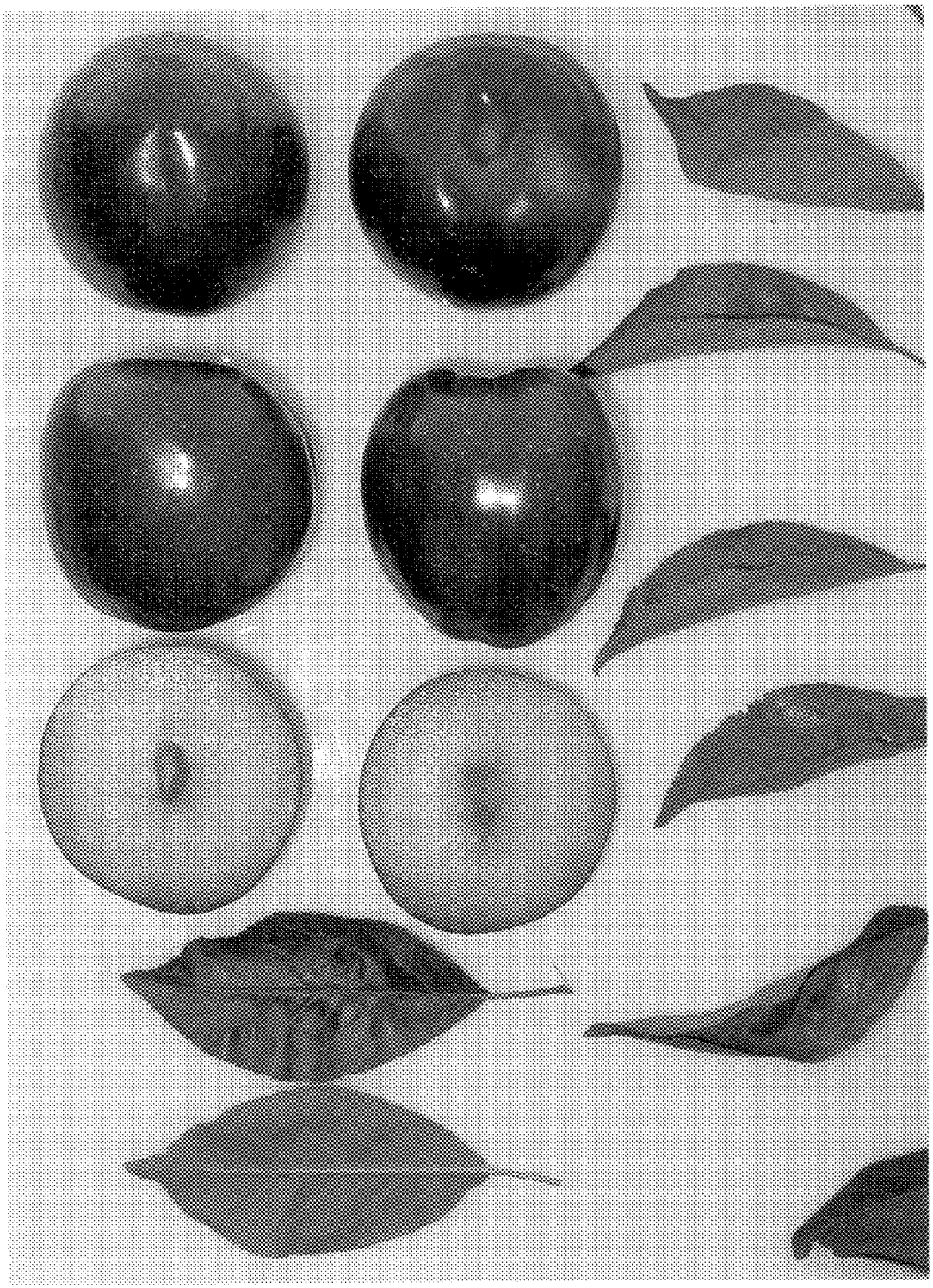

* * * * *